US008957371B2

(12) United States Patent
Haustein et al.

(10) Patent No.: US 8,957,371 B2
(45) Date of Patent: Feb. 17, 2015

(54) PRODUCING IMAGES OF A SPECIMEN (75) Inventors: Elke Haustein, Sulzbach-Laufen (DE); Wolfram Bühler, Hermaringen (DE); Camille Stebler, Fehren (CH); Holger Dömer, Bopfingen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 13/065,331

(22) Filed: Mar. 18, 2011

(65) Prior Publication Data

US 2011/0292385 A1 Dec. 1, 2011

(30) Foreign Application Priority Data

Mar. 19, 2010 (DE) .......................... 10 2010 003 056

(51) Int. Cl.
*G01N 23/225* (2006.01)
*G01N 1/30* (2006.01)
*B82Y 30/00* (2011.01)
(Continued)

(52) U.S. Cl.
CPC ............ *G01N 23/2251* (2013.01); *B82Y 30/00* (2013.01); *H01J 37/28* (2013.01); *H01J 37/3053* (2013.01); *H01J 37/3178* (2013.01); *G01N 1/31* (2013.01); *H01J 2237/2067* (2013.01); *H01J 2237/2809* (2013.01)
USPC ........................................................ 250/307

(58) Field of Classification Search
CPC ................................................... H01J 37/3178
USPC ............................................. 250/306–443.1
See application file for complete search history.

(56) References Cited

U.S. PATENT DOCUMENTS 5,149,974 A * 9/1992 Kirch et al. ................. 250/492.2
6,204,178 B1 * 3/2001 Marsh .......................... 438/686
(Continued)

FOREIGN PATENT DOCUMENTS

EP 1 890 136 A1 2/2008
EP 1 890 137 A1 2/2008
(Continued)

OTHER PUBLICATIONS

Griffith, 'Osmium Tetroxide and Its Applications' Platinum Metals Review, 1974, vol. 18, No. 3, p. 94-96.*
(Continued)

*Primary Examiner* — Jack Berman
*Assistant Examiner* — Eliza Osenbaugh-Stewart
(74) *Attorney, Agent, or Firm* — Muirhead and Saturnelli, LLC (57) ABSTRACT Producing images of a specimen includes introducing a specimen into a specimen chamber of a particle-beam device, selecting a specific position on the surface of the specimen, supplying a contrast-agent precursor on the specific position, providing a particle beam and/or a light beam, guiding the particle beam and/or the light beam onto the specific position, applying a contrast-agent layer to the specific position as a result of the interaction of the particle beam and/or the light beam with the contrast-agent precursor, leaving the contrast-agent layer on the surface of the specimen for a predetermined amount of time. During the predetermined amount of time, a first part of the contrast-agent layer diffuses into the specimen and a second part of the contrast-agent layer remains on the surface of the specimen. The specimen is imaged using an optical device and/or a particle-optical device and/or using the particle beam.

30 Claims, 7 Drawing Sheets (51) Int. Cl.
*H01J 37/28* (2006.01)
*H01J 37/305* (2006.01)
*H01J 37/317* (2006.01)
*G01N 1/31* (2006.01)

(56) References Cited

U.S. PATENT DOCUMENTS

| | | | |
|---|---|---|---|
| 6,881,955 B2 | 4/2005 | Lu et al. | |
| 7,297,944 B2 | 11/2007 | Kodama et al. | |
| 7,317,188 B2* | 1/2008 | Zhang et al. | 250/307 |
| 8,163,145 B2* | 4/2012 | Nadeau et al. | 204/298.36 |
| 2003/0198755 A1* | 10/2003 | Shichi et al. | 427/596 |
| 2004/0262518 A1 | 12/2004 | Lu et al. | |
| 2006/0008929 A1 | 1/2006 | Roy | |
| 2007/0045560 A1 | 3/2007 | Takahashi et al. | |
| 2008/0088831 A1* | 4/2008 | Mulders et al. | 356/237.2 |
| 2009/0052486 A1* | 2/2009 | Tamamori et al. | 372/41 |
| 2010/0092070 A1* | 4/2010 | Young et al. | 382/151 |
| 2011/0031394 A1* | 2/2011 | Knowles et al. | 250/307 |
| 2011/0204230 A1* | 8/2011 | Fujiwara | 250/311 |

FOREIGN PATENT DOCUMENTS

| | | |
|---|---|---|
| EP | 2 068 160 A2 | 6/2009 |
| JP | H10241618 A | 9/1998 |

OTHER PUBLICATIONS

J. Gierak, "Focused ion beam technology and ultimate applications," Semicond. Sci. Technol. 24 (2009), pp. 1-23.

Zeiss, "Discover New Horizons in Nan Scale Imaging—Zeiss Orion Plus," Oberkochen, Germany, Jul. 2009, 12 pp.

Zeiss, "Orion Plus—Spectra—Backscatter Spectroscopy for the Helium Ion Microscope," Oberkochen, Germany, Feb. 2009, 2 pp.

A. J. Ewald, et al., "Surface Imaging Microscopy, An Automated Method for Visualizing Whole Embryo Samples in Three Dimensions at High Resolution," Developmental Dynamics 225 (2002), pp. 369-375.

Y. Nagato, et al., "Observation on Backscattered Electron Image (BEI) of a Scanning Electron Microscope (SEM) in Semi-thin Sections Prepared for Light Microscopy," Tokai J Exp Clin Med., vol. 8, No. 2 (1983), pp. 167-174.

Ludwig Reimer, "Transmission Electron Microscopy: Physics of Image Formation and Microanalysis," Springer-Verlag, Berlin, 1984, pp. 5-8 and 86-134.

* cited by examiner

PRODUCING IMAGES OF A SPECIMEN

TECHNICAL FIELD

This application relates to a method and system for producing images of a specimen, more particularly an organic specimen.

BACKGROUND OF THE INVENTION

Electron-beam devices, more particularly a scanning electron microscope (also referred to as an SEM in the following text) and/or a transmission electron microscope (also referred to as a TEM in the following text), are used to examine objects (specimens) for obtaining information with respect to the properties and the behavior in specific conditions.

In an SEM, an electron beam (also referred to as a primary electron beam in the following text) is generated using a beam generator and focused on an object to be examined by a beam-guiding system. A deflection apparatus is used to guide the primary electron beam in a raster over a surface of the object to be examined. In doing so, the electrons of the primary electron beam interact with the object to be examined. As a result of the interaction, in particular electrons are emitted by the object (so-called secondary electrons) and electrons in the primary electron beam are scattered back (so-called backscattered electrons). The secondary electrons and backscattered electrons are detected and used to produce an image. Thus, an image is obtained of the object to be examined.

In the case of a TEM, a primary electron beam is likewise generated using a beam generator and focused on an object to be examined using a beam-guiding system. The primary electron beam penetrates the object to be examined. As the primary electron beam passes through the object to be examined, the electrons in the primary electron beam interact with the material of the object to be examined. The electrons that passed through the object to be examined are imaged on a fluorescent screen or on a detector (e.g. a camera) using a system including an objective and a projection lens. Here, imaging can also occur in the scanning mode of a TEM. Such a TEM is generally referred to as a STEM. Additionally, in order to image an object to be examined, provision can be made for a further detector for detecting electrons that are scattered back from the object to be examined and/or secondary electrons that are emitted by the object to be examined.

Furthermore, the prior art has disclosed the use of combination devices, in which both electrons and ions can be guided onto an object to be examined, for examining objects. By way of example, it is known to equip an SEM with an ion-beam column as well. Ions are generated using an ion-beam generator arranged in the ion-beam column and are used for preparing an object (for example for ablating material from the object or for depositing material on the object) or else for imaging. The SEM here serves in particular for observing the preparation, but also for the further examination of the prepared or unprepared object.

There are specimens that, as a result of the material properties thereof, only allow imaging with a low contrast, when imaged using a particle-beam device or a light-optical device. By way of example, these specimens include organic specimens, more particularly biological material. In order to increase the contrast when imaging such a specimen, the prior art has disclosed the practice of staining such a specimen. By way of example, such a specimen is immersed into a diluted solution of osmium tetroxide or ruthenium tetroxide. The specimen remains in the solution for a certain amount of time. The specimen may remain in the solution for a duration of between several minutes and a number of hours. The specimen is subsequently taken out of the solution and washed in order to remove excess osmium tetroxide or ruthenium tetroxide, which has not combined with the specimen. However, the above-described procedure for staining the specimen is complicated.

As mentioned previously, combination devices are known that provide both an electron beam and an ion beam. In particular, the prior art has disclosed the use of a particle-beam device that is equipped with both an electron-beam column and an ion-beam column. The electron-beam column provides an electron beam, which is focused onto a specimen. Here the specimen is arranged in a specimen chamber, in which there is a vacuum. The ion-beam column provides an ion beam, which is likewise focused onto the specimen. The ion beam is used, for example, to remove a surface layer. Once the surface layer of the specimen has been removed, a further surface of the specimen is uncovered. A gas injection system is used to admit a precursor substance (precursor) of a stain (contrast agent), namely gaseous osmium tetroxide, into the specimen chamber. The further surface of the specimen is stained as a result of the interaction of the ion beam with the gaseous osmium tetroxide. In the process, a layer of osmium or an osmium-containing layer is substantially deposited on the further surface. The process of staining is completed by stopping the supply of the gaseous osmium tetroxide into the specimen chamber. Furthermore, osmium tetroxide remaining in the specimen chamber is pumped away. This is followed by imaging the further surface. The known method provides for a repetition of the above-described steps. Thus, a layer is once again removed from the surface until a further surface is uncovered in turn. This further surface is stained in turn and imaged using the electron beam.

However, the aforementioned prior art is disadvantageous in that the layer thickness of the contrast-agent layer respectively deposited on the surface can be embodied such that it may be difficult to examine structures of the specimen that are situated under a thick contrast-agent layer. Furthermore, the known methods always stain the whole surface of the specimen, particularly when the specimen is immersed. However, it is desirable to modify the contrast of only a very specific confined region of the surface of the specimen.

The prior art has also disclosed a measurement method for a semiconductor, in which provision is made for increasing a contrast in an image. In the known measurement method, material is removed from a semiconductor substrate using a focused ion beam in order to uncover a surface. When the material is removed using the focused ion beam, reaction products are created, which redeposit on the uncovered surface. However, this leads to a reduction in the contrast. In order to improve the contrast, the surface of the semiconductor substrate uncovered by the focused ion beam is simultaneously supplied with a fluorine-containing gas and a high-energy beam. This removes the reaction products that redeposit on the surface of the semiconductor substrate. This increases the contrast.

With respect to the prior art, reference is made to EP 1 890 136 A1, EP 1 890 137 A1 and U.S. Pat. No. 6,881,955 B2, which are incorporated herein by reference.

Accordingly, it would be desirable to specify a method for producing an image of a specimen, which allows an imaging of, where possible, all structures in a specimen with a sufficiently high contrast and which can be performed easily.

SUMMARY OF THE INVENTION

According to the system described herein, a method produces images of a specimen, more particularly an organic specimen. In the method according to the system described herein, a specimen may be introduced into a specimen chamber of a particle-beam device. By way of example, there may be a vacuum in the specimen chamber. Furthermore, a specific position or a specific confined region on the surface of the specimen may be selected. A gaseous contrast-agent precursor may be supplied to this specific position or to this specific confined region on the surface. Here, both previously and in the following text, a contrast-agent precursor may be understood to mean a precursor substance of a contrast agent, which is applied to the specimen. Moreover, there is the provision of a particle beam and/or a light beam within the scope of the method according to the system described herein. The particle beam and/or the light beam may be guided onto the specific position or into the specific confined region on the surface of the specimen. A contrast-agent layer may be applied to the surface of the specimen at the specific position or in the specific confined region as a result of an interaction of the particle beam and/or the light beam with the free gaseous contrast-agent precursor or with the contrast-agent precursor adsorbed on the surface of the specimen. Hence there may be a local application of the contrast-agent layer. By way of example, the contrast-agent layer may be applied to a region of up to 150 µm, for example of up to 50 µm or of up to 5 µm around the specific position on the surface of the specimen. The aforementioned values should merely be understood as being exemplary. The system described herein is in no way restricted to these. The aforementioned values may be selected to be greater or else smaller. Further possible values are specified below. Furthermore, there are no restrictions on the shape of the specific confined region. Rather, the shape of the specific confined region may be selected as desired in the method according to the system described herein. Hence the contrast-agent layer may have any suitable geometric design.

The contrast-agent layer may be left on the surface for a predetermined amount of time. This predetermined amount of time may be selected such that a first part of the contrast-agent layer diffuses into the specimen. However, a second part of the contrast-agent layer may remain on the surface of the specimen. The specimen may subsequently be imaged using an optical device, a particle-optical device and/or the particle beam. By way of example, use is made of an electron-beam device, more particularly an SEM or a TEM. By way of example, the specimen may be embodied as a TEM lamella, which may be inserted into a TEM for further examinations.

An advantage of the system described herein is that the point of application of the contrast-agent layer to the surface of the specimen may be specified. Thus there may be a local application of the contrast-agent layer. By way of example, it is possible to cover only a very specific first region on the surface of the specimen with the contrast-agent layer, while a second region on the surface of the specimen is not covered by the contrast-agent layer. This second (unstained) region may then be available for, e.g., control measurements or for further examinations. By way of example, this allows comparison measurements to be made between the first (stained) region of the specimen and the second (unstained) region of the specimen.

A further advantage of the system described herein is that the staining of the specimen may be maintained due to the diffusion of the contrast agent into the specimen, and so a sufficiently high contrast may be achieved when imaging the specimen. Moreover, the contrast achieved by the method according to the system described herein may be influenced by the selection of the predetermined amount of time, and thus by influencing the degree of the diffusion of the contrast agent into the specimen.

A specimen treated thus may be examined more closely in a TEM. This affords the possibility of localizing the first part of the contrast-agent layer, which has diffused into the specimen. Hence, the distribution of the first part of the contrast-agent layer may be determined and imaged. In particular, the preparation and examination of a plurality of slices of the specimen for example may also allow a three-dimensional representation.

An embodiment of the method according to the system described herein may have the aforementioned features. Provision may additionally be made for the second part of the contrast-agent layer to be removed using the particle beam and for the first part of the contrast-agent layer to remain in the specimen. Additionally, or as an alternative thereto, provision may also be made for the following embodiment. In this embodiment, a specimen may likewise be introduced into a specimen chamber of a particle-beam device. By way of example, there may be a vacuum in the specimen chamber. Furthermore, a gaseous contrast-agent precursor may be supplied to a surface of the specimen. Moreover, there may be provision of a particle beam and/or a light beam. The particle beam and/or the light beam may be guided to the surface of the specimen. A contrast-agent layer may be applied to the surface of the specimen as a result of an interaction of the particle beam and/or the light beam with the gaseous contrast-agent precursor. This contrast-agent layer may be left on the surface for a predetermined amount of time. This predetermined amount of time may be selected such that a first part of the contrast-agent layer diffuses into the specimen. However, a second part of the contrast-agent layer may remain on the surface of the specimen. After the predetermined amount of time is up, the second part of the contrast-agent layer may be removed using the particle beam and the first part of the contrast-agent layer may remain in the specimen. In this respect, it is only the second part of the contrast-agent layer that has not diffused into the specimen that may be removed from the specimen. The specimen is subsequently imaged using an optical device, a particle-optical device and/or using the particle beam. By way of example, use is made of an electron-beam device, more particularly an SEM or a TEM. By way of example, the specimen may be embodied as a TEM lamella, which may be inserted into a TEM for further examination.

The aforementioned embodiments are advantageous in that it is only the second part of the contrast-agent layer, which does not diffuse into the specimen, that may be removed. Accordingly, this prevents structures on the surface of the specimen from being covered such that they cannot be imaged. However, reference is explicitly made to the fact that part of the contrast-agent layer may also remain on the specimen surface such that the specimen structures to be examined are not damaged by the ion beam or the light beam. However, the supply of suitable gases may also allow local selective etching of material by the ion beam or the light beam, and so there is no damage of the specimen structures to be examined. Provision may also be made for embodiments in which the second part of the contrast-agent layer is not completely removed from the surface of the specimen, but rather in which a certain layer thickness of the second part of the contrast-agent layer may remain on the surface of the specimen. However, this layer thickness may be selected such that structures arranged under the remaining second part of the contrast-agent layer may still be imaged. By way of example, the layer thickness in this case may lie in the region of between 1 nm and 500 nm or else in the region of between 1 nm and 100 nm, or in the region of between 1 nm and up to 50 nm or in the region of between 1 nm and up to 10 nm. Some exemplary embodiments of the system described herein for example provide for a layer thickness of approximately 10 nm.

In a further embodiment of the method according to the system described herein, the surface of the specimen may additionally or alternatively be provided with a first surface region and a second surface region, wherein the first surface region does not adjoin the second surface region. This embodiment is particularly advantageous if the specimen to be examined has a first side and a second side (for example a front side and a rear side, which is opposite to the front side). By way of example, the first surface region may be arranged on the first side and the second surface region may be arranged on the second side. Both the first surface region and the second surface region may be treated by the method according to the system described herein. In order to apply the method according to the system described herein, provision may for example be made for the specimen to be examined to be moved such that the first surface region is treated in a first position of the specimen to be examined and that the second surface region is treated in a second position of the specimen to be examined. In an alternative embodiment, provision may be made for the first surface region and the second surface region to adjoin one another. By way of example, this is the case if the specimen for example has a wedge-like shape, with the first surface region and the second surface region respectively forming one face of the wedge, which faces converge.

In a further embodiment of the method according to the system described herein, the particle beam and/or the light beam may additionally or alternatively be guided away from the surface of the specimen (for example from the aforementioned specific position) after the application of the contrast-agent layer. This may be provided in particular for stopping the interaction of the particle beam and/or the light beam with the free gaseous contrast-agent precursor or with the contrast-agent precursor adsorbed on the surface of the specimen. This affords the possibility of influencing the thickness of the applied contrast-agent layer.

In a further embodiment of the method according to the system described herein, the contrast-agent layer applied to the specimen may, additionally or alternatively, be relatively thin. By way of example, the contrast-agent layer may be applied to the surface of the specimen with a layer thickness in the region of between 1 nm and 1000 nm or else in the region of between 1 nm and 100 nm or else in the region of between 1 nm and 50 nm or else in the region of between 1 nm and 5 nm. Some exemplary embodiments of the system described herein for example provide for a layer thickness of approximately 10 nm.

In a further exemplary embodiment of the method according to the system described herein, an image of the specimen may additionally or alternatively be recorded, for example using a spectroscopic method, the particle beam and/or the light beam. An image contrast may subsequently be determined using the recorded image. In particular, one embodiment of the method according to the system described herein provides for an image of the surface of the specimen to be recorded a number of times in succession using the optical device, the particle-optical device and/or the particle beam in order subsequently to determine the image contrast using each recorded image. By way of example, this may take place before the second part of the contrast-agent layer is removed. The image contrast, referred to both previously and in the following text, may for example be determined by the so-called Weber contrast or the so-called Michelson contrast. The Weber contrast $K_{Weber}$ is specified by the following equation:

$$K_{Weber}(t) = \frac{I_{MAX}(t)}{I_{MIN}(t)} - 1. \qquad \text{[Equation 1]}$$

The Michelson contrast $K_{Michelson}$ is specified by the following equation:

$$K_{Michelson}(t) = \frac{I_{MAX}(t) - I_{MIN}(t)}{I_{MAX}(t) + I_{MIN}(t)} - 1. \qquad \text{[Equation 2]}$$

Here, $I_{MAX}$ denotes the maximum intensity of an image or an image section measured at a specific time t. By contrast, $I_{MIN}$ denotes the minimum intensity of an image or an image section measured at a specific time t. This affords the possibility of monitoring the degree of diffusion (i.e. the degree of contrasting and staining). Hence, the application of a suitable stopping procedure, which ends the diffusion, affords the possibility of achieving a desired image contrast. In particular, provision may be made for determining the image contrast present at the time of the imaging for each image of the specimen. The contrasting and the diffusion may be stopped when the desired image contrast is obtained. To this end, the second part of the contrast-agent layer may be removed when the desired image contrast is reached.

In a further exemplary embodiment of the method according to the system described herein, the temperature of the specimen may additionally or alternatively be controlled in order to control the diffusion of the first part of the contrast-agent layer, which is temperature dependent, into the specimen. By way of example, the use of a specimen holder equipped with a heating device may be suitable for this purpose. The specimen to be examined may be arranged on the specimen holder. The heating device may influence the temperature of the specimen. Additionally, or as an alternative thereto, provision may for example be made for heating the specimen using a laser beam, for example using a laser beam in the infrared band.

In a further exemplary embodiment of the method according to the system described herein, provision may additionally or alternatively be made for the particle beam for example to have an energy of less than or equal to 1 keV. Thus, it has a low-energy embodiment. By way of example, provision may furthermore be made for the particle beam to be embodied as an ion beam or as an electron beam. More particularly, it may be embodied as a noble gas ion beam, for example as an argon ion beam. However, the system described herein is not restricted to an argon ion beam. Rather, any suitable particle beam may be utilized within the scope of the system described herein.

In another further exemplary embodiment of the method according to the system described herein, two particle beams may additionally or alternatively be provided. In this exemplary embodiment, the particle beam already mentioned above may be provided as a first particle beam. A second particle beam may be provided in addition thereto. Both the first particle beam and the second particle beam may have specific functions in this exemplary embodiment. Thus, contrast agent may be applied to the surface of the specimen and/or the second part of the contrast-agent layer may be removed from the surface of the specimen using the first particle beam. Both the application and the removal may be observed in this exemplary embodiment by imaging the specimen using the second particle beam. By way of example, the second particle beam may be provided as an electron beam. More particularly, provision may be made for using the electron beam of an SEM.

In another further exemplary embodiment of the method according to the system described herein, the gaseous contrast-agent precursor may additionally or alternatively be supplied as gaseous osmium tetroxide or as gaseous ruthenium tetroxide. Provision may additionally or alternatively be made for the light beam to be provided as a laser beam. Herein, the radiation energy of the laser beam may be utilized or the wavelength of the laser beam may be selected such that the photon energy achieved by the laser beam is matched to the binding energy of the gaseous contrast-agent precursor. This, for example, affords the possibility of splitting osmium tetroxide into osmium, osmium-containing reaction products and/or other reaction products. These reaction products may be adsorbing or may already be adsorbed on the surface of the specimen. By way of example, a laser beam may be selected with a wavelength in the region of between 0.1 μm and 250 μm. In particular, $CO_2$ lasers, excimer lasers, solid-state lasers, semiconductor lasers and dye lasers may be suitable lasers. However, the system described herein is not restricted to the aforementioned types of lasers. Rather, use can be made of any suitable laser. Again, provision may be made, additionally or as an alternative thereto, for the light beam to be provided as UV light, for example with a wavelength of between 1 nm and 400 nm.

The system described herein also relates to a method of production of a conducting layer on a specimen, more particularly an organic specimen. In the method according to the system described herein, provision may be made for introducing a specimen into a specimen chamber of a particle-beam device, wherein, for example, there may be a vacuum in the specimen chamber. Furthermore, a specific position on a surface may be selected and a gaseous metal precursor, for example gaseous osmium tetroxide or gaseous ruthenium tetroxide, may be supplied to the specific position on the surface of the specimen. Here, both previously and in the following text, a metal precursor is understood to mean a precursor substance of a metal, which is applied to the specimen. The method furthermore may provide for the provision of a noble gas ion beam. The noble gas ion beam may be guided onto the specific position on the surface of the specimen, wherein the noble gas ion beam may interact with the gaseous metal precursor such that a metal-containing layer is applied to the surface of the specimen. In particular, provision may be made for the metal-containing layer to be applied with a layer thickness of up to 1000 nm, for example of up to 100 nm, or for example up to 50 nm or for example up to 10 nm or for example up to 5 nm or for example up to 1 nm. Alternatively, or in addition thereto, provision may be made for the metal-containing layer to be applied in a region of up to 1000 μm, for example of up to 500 μm, or of up to 250 μm, or of up to 50 μm or of up to 25 μm or of up to 5 μm around the specific position on the surface of the specimen.

BRIEF DESCRIPTION OF THE DRAWINGS

Embodiments of the system described herein will be explained in more detail based on the figures, which are briefly describes as follows.

DETAILED DESCRIPTION OF VARIOUS EMBODIMENTS

Figure 1:
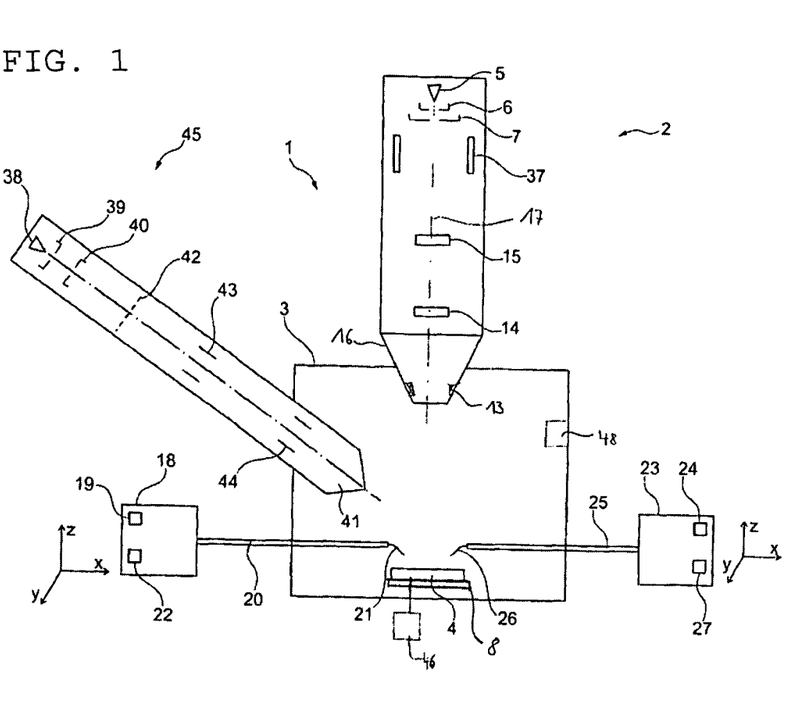
FIG. 1 shows a schematic illustration of an exemplary embodiment of a particle-beam device for carrying out the method according to the system described herein.

FIG. 1 shows a schematic illustration of a particle-beam device 1, using which the method according to the system described herein can be carried out. The particle-beam device 1 has two particle-beam columns, namely a first particle-beam column 2 and a second particle-beam column 45, which are arranged on a specimen chamber 3. The first particle-beam column 2 is embodied as an electron-beam column and is arranged vertically with respect to the specimen chamber 3.

The first particle-beam column 2 has a beam generator 5, in the form of an electron source (cathode), and a system consisting of a first electrode 6 and a second electrode 7. The second electrode 7 forms one end of a beam-guiding tube (not illustrated). By way of example, the beam generator 5 is embodied as a thermal field-emitter. Electrons emerging from the beam generator 5 are accelerated to a predefinable potential as a result of a potential difference between the beam generator 5 and the second electrode 7, and said electrons form the primary electron beam. The beam-guiding tube is guided through an opening of a magnetic lens, which acts as an objective 16. The objective 16 is provided with pole shoes (not illustrated), in which coils (not illustrated) are arranged. Furthermore, provision is made of a raster device 13, using which the primary electron beam is deflected and can be scanned over an object 4 arranged in the specimen chamber 3. The object 4 is arranged on an adjustable object holder 8. The object holder 8 is designed to be able to move in three orthogonal directions (x-direction, y-direction and z-direction). Furthermore, it can rotate about a first rotational axis and about a second rotational axis, with the first rotational axis and the second rotational axis being perpendicular to one another. Reference is explicitly made to the fact that, additionally or alternatively, the object holder 8 can also be moved along at least one further axis or can rotate about at least one further axis.

For the purposes of imaging, secondary electrons and/or back-scattered electrons, which are generated as a result of the interaction between the primary electron beam and the object 4, are detected by a detector arrangement in the particle-beam device 1. To this end, a first detector 14 is provided on the object side along the optical axis 17 of the first particle-beam column 2, while a second detector 15 is arranged on the source side along the optical axis 17 (that is to say in the direction of the beam generator 5). Both the first detector 14 and the second detector 15 are oriented in the direction of the object 4 or the space arranged in front of the object 4. Furthermore, the first detector 14 and the second detector 15 are arranged offset with respect to one another in the axial direction. Reference is explicitly made to the fact that the particle-beam device 1 can, additionally or alternatively, be provided with at least one further detector.

The second particle-beam column 45 is embodied as an ion-beam column and is arranged tilted at an angle of approximately 50° with respect to the first particle-beam column 2. The second particle-beam column 45 has an ion-beam generator 38. The ion-beam generator 38 generates ions, which form an ion beam. By way of example, the ion beam is formed from noble gas ions. More particularly, provision is made for the ion beam to be formed from argon ions. However, the system described herein is not restricted to argon ions. Rather, use can also be made of other types of ions, for example Ga-ions, Au-ions, Si-ions and/or He-ions.

The ions are accelerated to a predefinable potential using an extraction electrode 39. The ion beam then passes through an ion optical system in the second particle-beam column 45, wherein the ion optical system has a condenser lens 40 and an arrangement of further lenses 41. The lenses 41 (objective lens) generate a focused ion probe, which impinges onto the object 4. A selectable aperture 42, a first electrode arrangement 43 and a second electrode arrangement 44 are arranged above the lenses 41 (i.e. in the direction of the ion-beam generator 38), with the first electrode arrangement 43 and the second electrode arrangement 44 being designed as scanning electrodes.

The ion beam is scanned over the surface of the object 4 using the first electrode arrangement 43 and the second electrode arrangement 44, with the first electrode arrangement 43 acting in a first direction and the second electrode arrangement 44 acting in a second direction, which is opposite to the first direction. This brings about scanning in e.g. the x-direction. Scanning in a y-direction perpendicular thereto is brought about by additional electrodes (not illustrated), which are rotated by 90°, on the first electrode arrangement 43 and on the second electrode arrangement 44.

The second particle-beam column 45 has two functions. On the one hand, it can be used for imaging a region of interest on the surface of the object 4. Interaction particles are detected by the first detector 14 or the second detector 15. As an alternative thereto, provision is made for the interaction particles to be detected by a further detector (not illustrated). However, on the other hand, the second particle column also serves for processing the region of interest on the surface of the object 4.

Furthermore, on the specimen chamber 3, a light-beam device 48 is arranged, which can be used to guide a light beam onto the object 4. By way of example, the light-beam device 48 provides a laser beam, which for example has a wavelength in the region of between 0.1 μm and 250 μm. $CO_2$-lasers, excimer lasers, solid-state lasers, semiconductor lasers and dye lasers are particularly suitable as a light-beam device 48. However, the invention is not restricted to the aforementioned types of laser. Rather, use can be made of any suitable laser. Alternatively, or in addition thereto, provision is made for the light beam to be provided as UV light, for example with a wavelength of between 1 nm and 400 nm.

The particle-beam device 1 furthermore has a first gas supply unit 18, which serves for supplying a gaseous contrast-agent precursor (e.g. osmium tetroxide or ruthenium tetroxide) to a specific position on the surface of the object 4. Here, the gaseous contrast-agent precursor is held in a first gas storage system 19. The first gas supply unit 18 is provided with a first supply line 20, which projects into the specimen chamber 3. The first supply line 20 has a first cannula 21 in the direction of the object 4, which cannula can be brought into the vicinity of the specific position on the surface of the object 4, for example to within a distance of between 10 μm and 1 mm. The first cannula 21 has a supply opening, the diameter of which lies in the region of e.g. between 10 μm and 1000 μm, for example in the region of between 400 μm and 600 μm. The first gas supply unit 18 is furthermore provided with a first adjustment unit 22, which allows an adjustment of the position of the first cannula 21 in all three spatial directions (x-direction, y-direction, z-direction) and an adjustment of the orientation of the first cannula 21 by rotation and/or tilting.

In addition to the first gas supply unit 18, provision is made of a second gas supply unit 23, which is provided for supplying a precursor for a protective layer (referred to as a protective-layer precursor below) to the specific position on the surface of the object 4. The protective-layer precursor, for example a metal precursor, more particularly methylcyclopentadienyl(trimethyl) platinum (IV), serves for applying a protective layer to the object 4 in the case of an interaction with a particle beam or light beam such that partial regions on the surface of the object 4 are covered and protected. By way of example, this prevents contrast agent from diffusing into the object 4 in these partial regions. The protective-layer precursor is held in a second gas storage system 24. Furthermore, the second gas supply unit 23 is provided with a second supply line 25, which projects into the specimen chamber 3. The second supply line 25 has a second cannula 26 in the direction of the object 4, which cannula can be brought into the vicinity of the prescribable position on the surface of the object 4, for example to within a distance of between 10 μm and 1 mm. The second cannula 26 has a supply opening, the diameter of which lies in the region of e.g. between 10 μm and 1000 μm, for example in the region of between 400 μm and 600 μm. The second gas supply unit 23 is furthermore provided with a second adjustment unit 27, which allows an adjustment of the position of the second cannula 26 in all three spatial directions (x-direction, y-direction, z-direction) and an adjustment of the orientation of the second cannula 26 by rotation and/or tilting.

In further exemplary embodiments, the first gas storage system 19 of the first gas supply unit 18 and/or the second gas storage system 24 of the second gas supply unit 23 are/is not arranged directly on the first gas supply unit 18 and the second gas supply unit 23, respectively. Rather, provision is made in these further exemplary embodiments for the first gas storage system 19 and/or the second gas storage system 24 to be arranged on e.g. a wall of a room in which the particle-beam device 1 is located.

The first gas supply unit 18 serves for supplying the gaseous contrast-agent precursor, wherein the ion beam and the gaseous contrast-agent precursor interact on the specific position on the surface of the object 4 such that a contrast-agent layer is deposited on the specific point on the surface of the object 4. The same applies for the second gas supply unit 23. It serves for supplying the protective-layer precursor, wherein the ion beam and the protective-layer precursor interact on the specific position on the surface of the object 4 such that a protective layer is deposited on the specific point on the surface of the object 4.

Reference is made explicitly to the fact that the above-described gas supply units should merely be understood as being exemplary. The system described herein is not restricted to the above-described gas supply units. Rather, any suitable gas supply unit or any suitable gas supply units can be used within the scope of the invention, in particular a gas supply system with a number of gas supply units.

The object 4 is connected to a heating device 46 via the object holder 8. The heating device 46 affords the possibility of influencing the temperature of the object 4. This will be explained in more detail below.

Figure 2:
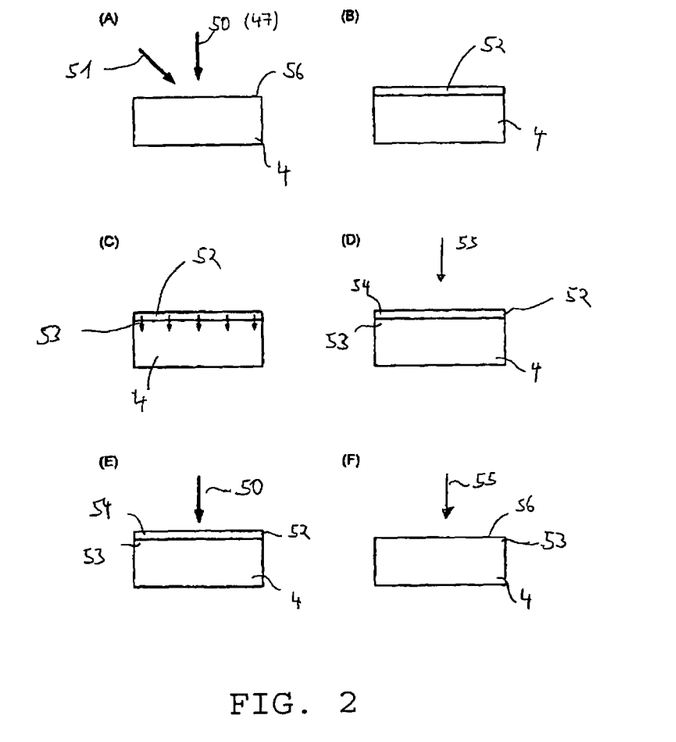
FIG. 2 shows a schematic illustration of a first exemplary embodiment of a method according to the system described herein.
Figure 7:
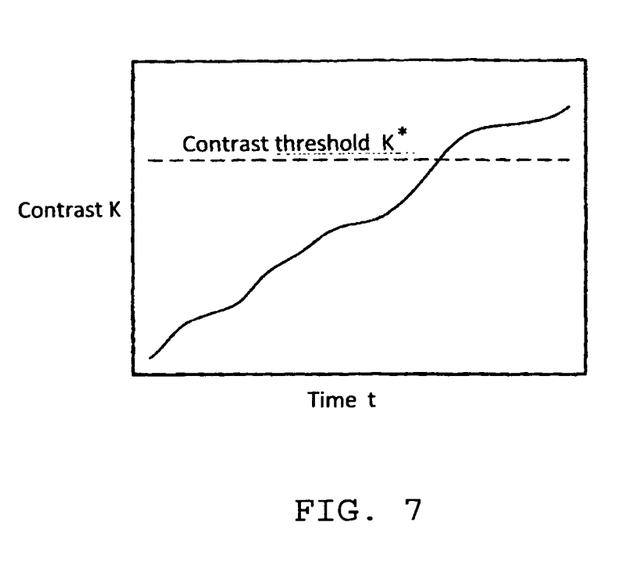
FIG. 7 shows a schematic illustration of an image contrast as a function of time.

FIG. 2 shows a first exemplary embodiment of the method according to the system described herein, which can be carried out using the particle-beam device 1 as per FIG. 1. First of all, an object 4 to be examined, for example an organic specimen, is introduced into the specimen chamber 3. There is a vacuum in the specimen chamber 3. A gaseous contrast-agent precursor 51 is then supplied to a surface 56 of the object 4. This gaseous contrast-agent precursor 51 is provided using the first gas supply unit 18. Moreover, an ion beam 50, which for example is formed from argon ions, is guided onto the surface 56 of the object 4 (cf. FIG. 2A). As an alternative thereto, it is also possible for an electron beam to be guided onto the surface 56 of the object 4. As another alternative thereto, provision is made for a light beam 47 to be guided onto the surface 56 of the object 4 via the light-beam device 48 (cf. FIG. 2A). Here, the object holder 8 is arranged such that the ion beam 50, the electron beam or the light beam 47 for example impinges perpendicularly onto the surface 56 of the object 4; however, the system described herein is not restricted to perpendicular incidence. Rather, other directions of incidence are also provided for within the scope of the system described herein. As a result of an interaction of the ion beam 50, the electron beam or the light beam 47 with the gaseous contrast-agent precursor 51, a contrast-agent layer 52 is deposited on the surface 56 of the object 4 (cf. FIG. 2B). The contrast-agent layer 52 has a layer thickness of, for example, up to 1000 nm, for example of up to 100 nm or for example up to 50 nm or for example up to 10 nm or for example up to 5 nm or for example up to 1 nm. The supply of the ion beam 50, the electron beam or the light beam 47, and the supply of the gaseous contrast-agent precursor 51 are subsequently stopped. The contrast-agent layer 52 is left on the object 4 for a predetermined amount of time such that a first part 53 of the contrast-agent layer 52 can diffuse into the object 4. A second part 54 of the contrast-agent layer 52 remains on the object 4 as a contrast-agent layer 52 (cf. FIGS. 2C and 2D). The diffusion of the first part 53 of the contrast-agent layer 52 can for example be influenced by controlling the temperature of the object 4. Furthermore, provision is made for the object 4 to be imaged a number of times in succession using an electron beam 55 (cf. FIG. 2D). As an alternative thereto, use can also be made of the ion beam. The image contrast in the image is determined in each image. This allows monitoring of the degree of the diffusion and hence the staining of the object 4 (contrasting procedure). As soon as a prescribed threshold of the image contrast is reached, the second part 54 of the contrast-agent layer 52 is removed in this exemplary embodiment such that further diffusion of the contrast agent into the object 4 is stopped. The dependence of the image contrast on time is illustrated in FIG. 7 in an exemplary fashion. There, the image contrast K is plotted as a function of time t. As illustrated, the image contrast K increases with time. The threshold is given by the contrast threshold K*. Stopping the diffusion into the object affords the possibility of obtaining images with a desired image contrast.

The second part 54 of the contrast-agent layer 52 is removed using, e.g., the ion beam 50 (cf. FIGS. 2E and 2F). To this end, the object holder 8 is moved such that the object 4 is suitably arranged, and so the ion beam 50 can easily be used for the removal. Here, the ion beam can be incident for example substantially perpendicular to the surface 56 or for example also substantially parallel to the surface 56. The object holder 8 is subsequently moved such that the electron beam 55 impinges e.g. perpendicularly or substantially perpendicularly onto the surface 56 of the object 4. As an alternative thereto, the electron beam 55 impinges onto the surface 56 of the object 4 from a direction that is aligned at an angle to the normal of the surface 56 of the object 4, which angle differs from 0° or 180°. The electron beam 55 is then used to image the object 4 and examine it more closely. Alternatively, or in addition thereto, the beam 55 in FIG. 2F can also be embodied as a light beam of an optical device (for example a light microscope). Again alternatively, or in addition thereto, use can also be made of the ion beam 50 for imaging the object 4.

In particular, the exemplary embodiment as per FIG. 2 is advantageous in that the second part 54 of the contrast-agent layer 52, which does not diffuse into the object 4, is removed such that substantially all structures of the object 4 can be identified. Furthermore, the staining of the object 4 using the contrast agent remains such that a sufficiently good contrast can be obtained when imaging the object 4. Moreover, the contrast can be adjusted in the method according to the system described herein by selecting an appropriate predetermined amount of time and hence by influencing the degree of diffusion of the contrast agent into the object 4.

Figure 3:
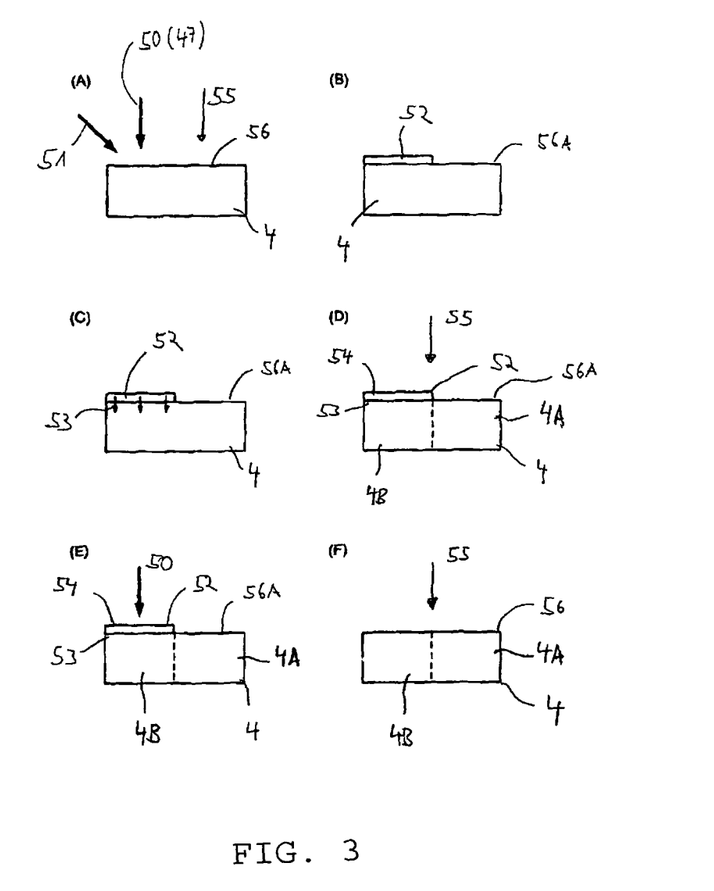
FIG. 3 shows a schematic illustration of a second exemplary embodiment of a method according to the system described herein.

FIG. 3 shows a second exemplary embodiment of the method according to the system described herein, which can be carried out using the particle-beam device 1 as per FIG. 1. In this exemplary embodiment, a contrast agent is applied to a specific position or a specific confined region on the surface 56 of the object 4. The exemplary embodiment as per FIG. 3 is based on the exemplary embodiment as per FIG. 2. Hence the same elements are denoted by the same reference signs. The object 4, for example an organic specimen, is firstly introduced into the specimen chamber 3. There is a vacuum in the specimen chamber 3. A specific position or a specific confined region on the surface 56 of the object 4 to which the contrast agent should be applied is identified using an image generated by e.g. the electron beam 55. The gaseous contrast-agent precursor 51 is then supplied to this specific position or this specific confined region on the surface 56 of the object 4. The gaseous contrast-agent precursor 51 is provided using the first gas supply unit 18. Moreover, the ion beam 50, which in turn is formed from e.g. argon ions, is also guided onto this specific position or this specific confined region on the surface 56 of the object 4 (cf. FIG. 3A). As an alternative thereto, provision is made for the electron beam to be guided onto this specific position or this specific confined region on the surface 56 of the object 4. Alternatively, or in addition thereto, provision is also made in this case for the light beam 47 to be guided onto the surface 56 of the object 4. Here, the object holder 8 is arranged such that the ion beam 50, the electron beam or the light beam 47 impinges e.g. perpendicularly or substantially perpendicularly onto the surface 56 of the object 4. As an alternative thereto, provision is made for the ion beam 50, the electron beam or the light beam 47 to impinge from a direction that is aligned at an angle to the normal of the surface 56 of the object 4, which angle differs from 0° or 180°. As a result of an interaction of the ion beam 50, the electron beam or the light beam 47 with the gaseous contrast-agent precursor 51, a contrast-agent layer 52 is deposited on the surface 56 of the object 4 (cf. FIG. 3B). However, the contrast-agent layer 52 is only applied to the surface 56 of the object 4 at the specific position or in the specific confined region. A partial region 56A of the surface 56 is not covered by the contrast agent (cf. FIG. 3B). The contrast-agent layer 52 in this case also has a layer thickness of e.g. up to 1 µm, of up to 500 nm, of up to 50 nm, of up to 10 nm or of up to 5 nm or even of up to 1 nm. By way of example, the contrast-agent layer 52 is applied in a region of up to 1000 µm or of up to 500 µm or of up to 250 µm or of up to 50 µm or of up to 25 µm or of up to 5 µm around the specific position on the surface 56 of the object 4. In the process, the region can be selected to have any shape. The supply of the ion beam 50, the electron beam or the light beam 47, and the supply of the gaseous contrast-agent precursor 51 are subsequently stopped. The contrast-agent layer 52 is left on the object 4 for a predetermined amount of time such that the first part 53 of the contrast-agent layer 52 diffuses into the object 4. By way of example, the diffusion can be influenced by controlling the temperature of the object 4 using the heating device 46. The second part 54 of the contrast-agent layer 52 remains on the object 4 as a contrast-agent layer 52 (cf. FIGS. 3C and 3D). Firstly, a first region 4A of the object 4 into which no contrast agent has diffused and, secondly, a second region 4B of the object 4 into which the first part 53 of the contrast-agent layer 52 has diffused are created. In this exemplary embodiment, the image contrast of the image is also determined by imaging the object 4 a number of times in succession using the electron beam 55 or the ion beam (cf. FIG. 3D), as explained previously. To this end, the object holder 8 is moved such that the electron beam 55 or the ion beam impinges perpendicularly or substantially perpendicularly onto the object 4. As an alternative thereto, provision is made for the electron beam 55 or the ion beam to impinge from a direction that is aligned at an angle to the normal of the surface 56 of the object 4, which angle differs from 0° or 180°.

The second part 54 of the contrast-agent layer 52 is removed when the desired image contrast is reached. The second part 54 of the contrast-agent layer 52 is removed using the ion beam 50 (cf. FIGS. 3E and 3F). As an alternative thereto, the second part 54 of the contrast-agent layer 52 can also be removed by gas-assisted particle-beam etching. In order to remove the second part 54 of the contrast-agent layer 52, the object holder 8 is moved such that the ion beam 50 impinges onto the object 4 in a suitable manner. The surface 56 of the object 4 is then imaged using the electron beam 55 for inspection purposes. To this end, the object holder 8 is moved such that the electron beam 55 impinges e.g. perpendicularly or substantially perpendicularly onto the surface 56 of the object 4. As an alternative thereto, provision is made for the electron beam 55 to impinge from a direction that is aligned at an angle to the normal of the surface 56 of the object 4, which angle differs from 0° or 180°. Alternatively, or in addition thereto, the beam 55 of FIG. 3F can in this exemplary embodiment also be embodied as a light beam of an optical device, using which e.g. the surface 56 is then imaged. Again alternatively, or in addition thereto, use can also be made of the ion beam 50 for imaging the object 4.

In addition to the advantages already specified with respect to FIG. 2, the exemplary embodiment as per FIG. 3 has the additional advantage that the contrast agent is applied to a specific position or a specific confined region on the surface 56 of the object 4. Thus there is a locally determined application of the contrast agent. In the illustrated exemplary embodiment, it is only the second part 4B of the object 4 that is covered by the contrast agent (in other words, it is only the second part 4B of the object 4 that is stained), while the first part 4A of the object 4 is not, or substantially not, covered by the contrast agent. The non-stained first part 4A of the object 4 can for example be used for comparison measurements between the first part 4A of the object 4 and the second part 4B of the object 4.

Figure 4:
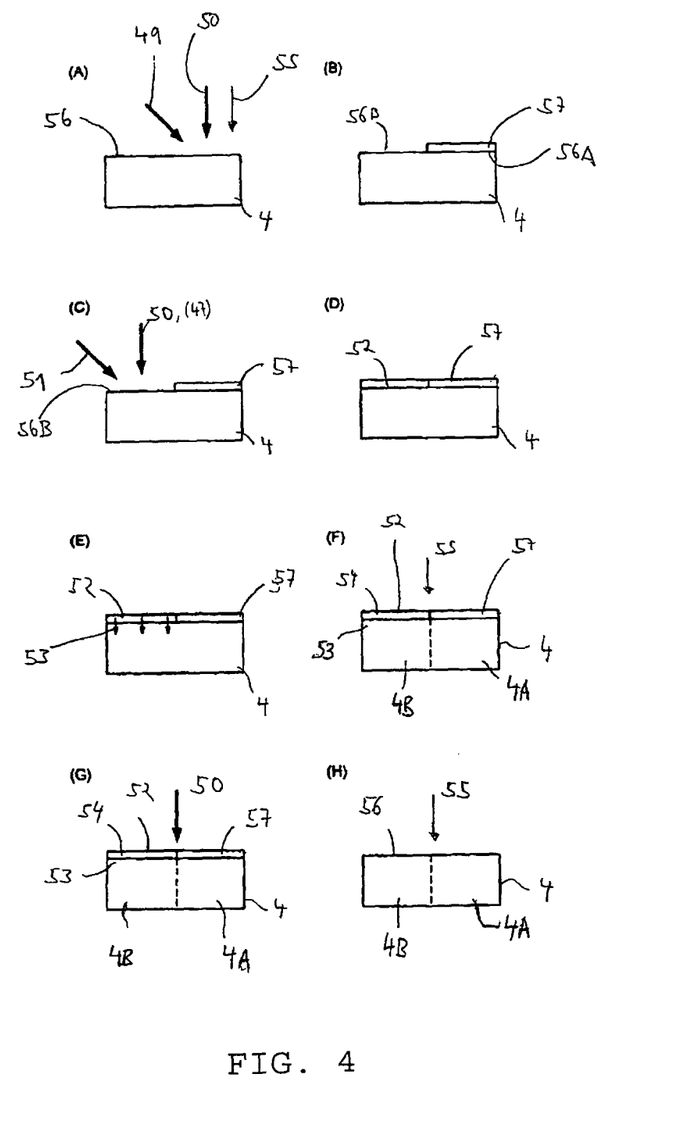
FIG. 4 shows a schematic illustration of a third exemplary embodiment of a method according to the system described herein.

FIG. 4 shows a third exemplary embodiment of the method according to the system described herein, which can be carried out using the particle-beam device 1 as per FIG. 1. The exemplary embodiment as per FIG. 4 is similar to the exemplary embodiment in FIG. 3. The object 4, for example an organic specimen, is firstly introduced into the specimen chamber 3. There is a vacuum in the specimen chamber 3. A region on the surface 56 of the object 4, to which a protective layer should be applied, is identified using an image of the surface 56 of the object 4, generated by the electron beam 55. A protective-layer precursor 49 is firstly guided to this region. The protective-layer precursor 49 is provided using the second gas supply unit 23. Moreover, the ion beam 50, which in turn is formed from e.g. argon ions, is also guided onto the aforementioned region on the surface 56 of the object 4 (cf. FIG. 4A). As a result of an interaction of the ion beam 50 with the protective-layer precursor 49, the protective layer 57 (for example a metal-containing layer) is applied to a first partial region 56A of the surface 56 of the object 4 (cf. FIG. 4B). Alternatively, or in addition thereto, use can also be made of the electron beam or the light beam for applying the protective layer 57. A second partial region 56B of the surface 56 of the object 4 is not covered by a protective layer.

Subsequently, the contrast-agent layer 52 now is deposited on the second partial region 56B of the surface 56 of the object 4 (cf. FIG. 4C). To this end, the gaseous contrast-agent precursor 51 is now supplied to the second partial region 56B on the surface 56 of the object 4. The gaseous contrast-agent precursor 51 is again provided using the first gas supply unit 18. Moreover, the ion beam 50, formed from e.g. argon ions, is guided onto the second partial region 56B of the surface 56 of the object 4 (cf. FIG. 4C). Here too, provision can alternatively or additionally be made for providing the light beam 47 or the electron beam. As a result of an interaction of the ion beam 50, the electron beam or the light beam 47 with the gaseous contrast-agent precursor 51, the contrast-agent layer 52 is deposited on the second partial region 56B of the surface 56 of the object 4 (cf. FIG. 4D). Both the protective layer 57 and the contrast-agent layer 52 for example have a layer thickness of up to 1 µm, of up to 500 nm, of up to 50 nm, of up to 10 nm, of up to 5 nm or else of up to 1 nm.

The supply of the ion beam 50 or the light beam 47, and the supply of the gaseous contrast-agent precursor 51 are subsequently stopped. The contrast-agent layer 52 is left on the object 4 for a predetermined amount of time such that a first part 53 of the contrast-agent layer 52 can diffuse into the object 4. A second part 54 of the contrast-agent layer 52 remains on the object 4 as the contrast-agent layer 52 (cf. FIGS. 4E and 4F). Firstly, a first region 4A of the object 4 into which no contrast agent has diffused and, secondly, a second region 4B of the object 4 into which the first part 53 of the contrast-agent layer 52 has diffused are created. By way of example, the diffusion can also be influenced in this case by controlling the temperature of the object 4 using the heating device 46. In this exemplary embodiment, a plurality of images can be recorded by imaging the object 4 a number of times in succession using the electron beam 55 (cf. FIG. 4F) and the respective image contrast can be determined therefrom. The diffusion into the object can be stopped when a desired image contrast is reached, as explained previously. For the purposes of imaging the object 4, the object 4 is positioned using the object holder 8 such that the electron beam 55 impinges perpendicularly or substantially perpendicularly onto the surface 56 of the object 4. As an alternative thereto, provision is made for the electron beam 55 to impinge from a direction that is aligned at an angle to the normal of the surface 56 of the object 4, which angle differs from 0° or 180°.

As soon as the desired image contrast is reached, both the protective layer 57 and the second part 54 of the contrast-agent layer 52 are removed using the ion beam 50 (cf. FIGS. 4G and 4H). To this end, the object holder 8 is moved such that the ion beam 50 impinges onto the object 4 in a suitable fashion. As an alternative thereto, the removal can also take place using gas-assisted particle-beam etching.

The surface 56 of the object 4 is subsequently imaged using the electron beam 55. To this end, the object holder 8 is moved such that the electron beam 55 impinges perpendicularly or substantially perpendicularly onto the object 4. As an alternative thereto, provision is made for the electron beam 55 to impinge from a direction that is aligned at an angle to the normal of the surface 56 of the object 4, which angle differs from 0° or 180°. Alternatively, or in addition thereto, the beam 55 of FIG. 4H can in this exemplary embodiment also be embodied as a light beam of an optical device, using which the surface 56 is then imaged. Again alternatively, or in addition thereto, use can also be made of the ion beam 50 for imaging the surface 56. This exemplary embodiment affords the possibility of using the first part 4A of the object 4 for comparison measurements between the first part 4A of the object 4 and the second part 4B of the object 4.

Figure 5:
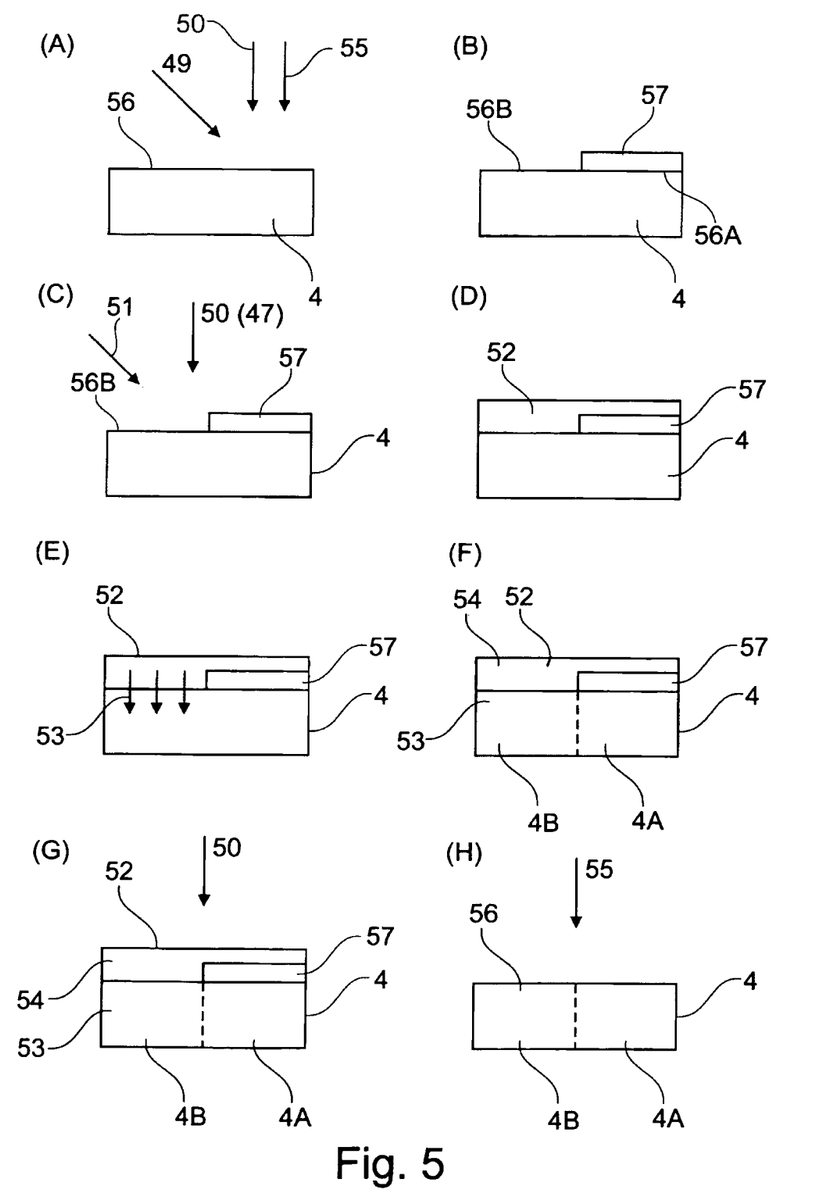
FIG. 5 shows a schematic illustration of a slightly modified embodiment of the third exemplary embodiment as per FIG. 4.

FIG. 5 shows a modification of the third exemplary embodiment as per FIG. 4. The same elements are denoted by the same reference signs. The modification as per FIG. 5 only differs from the third exemplary embodiment as per FIG. 4 in that the contrast-agent layer 52 at least partly, or even entirely, overlaps the protective layer 57, with the protective layer 57 preventing diffusion of contrast agent into the object 4 in the region of the protective layer 57.

Figure 6:
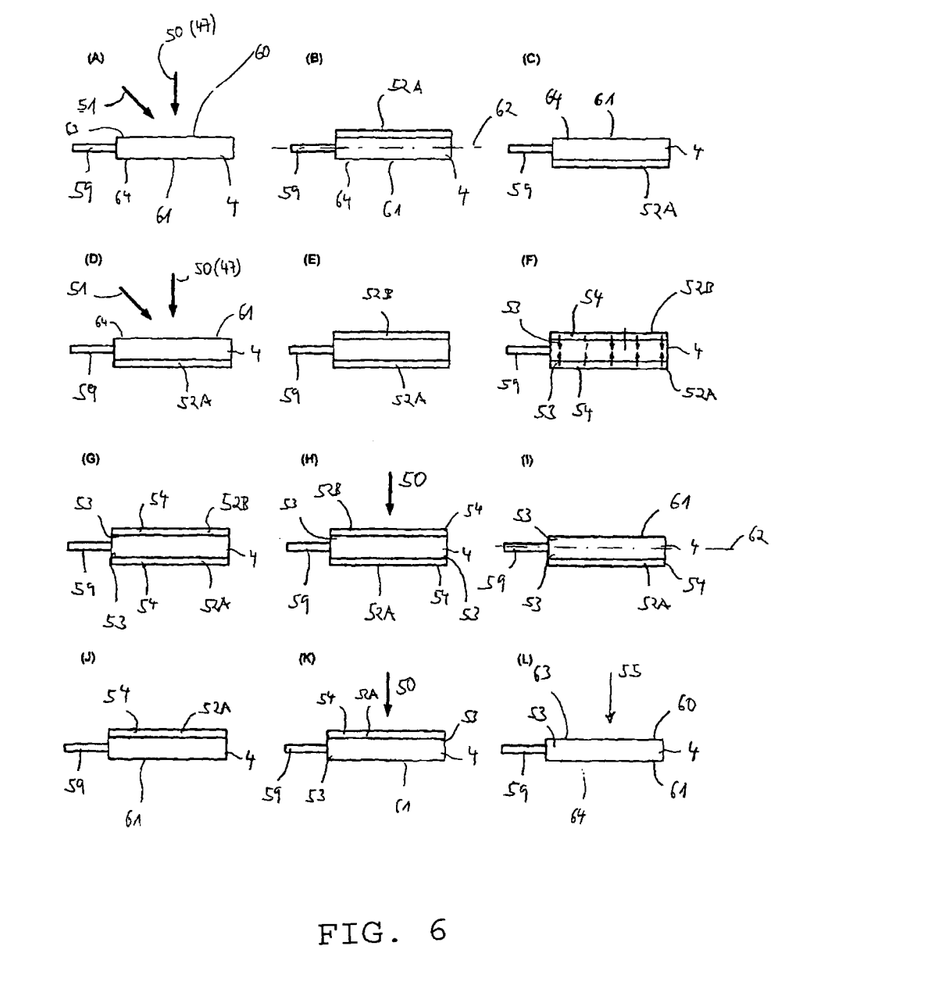
FIG. 6 shows a schematic illustration of a fourth exemplary embodiment of a method according to the system described herein.

FIG. 6 shows a fourth exemplary embodiment of the method according to the system described herein, which can be carried out using the particle-beam device 1 as per FIG. 1. In this exemplary embodiment, the object 4 is embodied as a TEM lamella and treated by the method according to the system described herein. The object 4 is arranged on a holder 59, which in turn is connected to the object holder 8 (not illustrated). The object 4 (for example an organic specimen) is once again firstly introduced into the specimen chamber 3. The object 4 has a first surface region 60 on a first side 63 of the object 4. Furthermore, the object 4 has a second surface region 61 on a second side 64 of the object 4. The first surface region 60 does not adjoin the second surface region 61 (cf. FIG. 6A). In an alternative embodiment, provision is made for the first surface region 60 to adjoin the second surface region 61. By way of example, this is the case if the object 4 for example has a wedge-like shape, with the first surface region 60 and the second surface region 61 respectively forming one face of the wedge, which faces converge.

A first contrast-agent layer 52A is first of all deposited on the first surface region 60 of the object 4. To this end, the gaseous contrast-agent precursor 51 is supplied to the first surface region 60 of the object 4. The gaseous contrast-agent precursor 51 is once again provided using the first gas supply unit 18. Moreover, the ion beam 50, formed from e.g. argon ions, is guided onto the first surface region 60 of the object 4 (cf. FIG. 6A). Here, alternatively or additionally, the light beam 47 may also be provided. As a result of an interaction of the ion beam 50 or the light beam 47 with the gaseous contrast-agent precursor 51, the first contrast-agent layer 52A is deposited on the first surface region 60 of the object 4 (cf. FIG. 6B).

The supply of the ion beam 50 or the light beam 47, and the supply of the gaseous contrast-agent precursor 51 are subsequently stopped. Then the object 4 is rotated by substantially 180° about the first rotational axis, provided with reference sign 62 in FIG. 5B, using the object holder 8 such that the ion beam 50 or the light beam 47 and the gaseous contrast-agent precursor 51 can be supplied to the second surface region 61 of the object 4 (cf. FIGS. 6C and 6D). In the case of a wedge-like design of the object 4, the object 4 is rotated in such a suitable fashion that the ion beam 50 or the light beam 47 and the gaseous contrast-agent precursor 51 can be supplied to the second surface region 61 of the object 4. As a result of the interaction of the ion beam 50 or the light beam 47 with the gaseous contrast-agent precursor 51, a second contrast-agent layer 52B is now deposited on the second surface region 61 of the object 4 (cf. FIG. 6E).

Both the first contrast-agent layer 52A and the second contrast-agent layer 52B have a layer thickness of up to 1000 nm, for example of up to 100 nm, or for example up to 50 nm or for example up to 10 nm or for example up to 5 nm or for example up to 1 nm.

The supply of the ion beam 50 or the light beam 47, and the supply of the gaseous contrast-agent precursor 51 onto the second surface 61 of the object 4 are subsequently stopped. Both the first contrast-agent layer 52A and the second contrast-agent layer 52B are left on the object 4 for a predetermined amount of time such that, from both the first contrast-agent layer 52A and the second contrast-agent layer 52B respectively, a first part 53 of the first and second contrast-agent layers 52A and 52B can diffuse into the object 4. A second part 54 of the first and second contrast-agent layers 52A and 52B remains on the object 4 as the first contrast-agent layer 52A and the second contrast-agent layer 52B (cf. FIGS. 6F and 6G).

After the diffusion process has been completed, the respective second part 54 of the first and second contrast-agent layers 52A and 52B is removed using the ion beam 50. The second part 54 of the contrast-agent layer 52B remaining as the second contrast-agent layer 52B is removed by removing the second contrast-agent layer 52B using the ion beam 50. As a result, the second surface region 61 of the object 4 is once again uncovered (cf. FIGS. 6H and 6I). The ion beam 50 is subsequently masked and the object 4 is rotated about the first rotational axis 62 using the object holder 8 such that the ion beam 50 can be guided onto the first contrast-agent layer 52A (cf. FIGS. 6I and 6J). The second part 54 of the contrast-agent layer 52A remaining as the first contrast-agent layer 52A is removed using the ion beam 50 such that the first surface region 60 of the object 4 is once again uncovered; this removal is brought about using the ion beam 50. The first parts 53 of the first and second contrast-agent layers 52A and 52B remain in the object 4. Reference is explicitly made to the fact that the system described herein is not restricted to the aforementioned sequence of steps when removing the two contrast-agent layers 52A and 52B. Rather, any suitable sequence may be applied. By way of example, provision is made in an alternative embodiment for first of all removing the first contrast-agent layer 52A and subsequently removing the second contrast-agent layer 52B. In yet another embodiment, provision is made for firstly removing a first part of the first contrast-agent layer 52A (or a first part of the second contrast-agent layer 52B) and subsequently removing a second part of the second contrast-agent layer 52B (or a second part of the first contrast-agent layer 52A).

The object 4 can then be examined in more detail using an electron beam, for example the aforementioned electron beam 55, or using an ion beam, for example an He-ion beam. In doing so, both the first surface region 60 and (after a corresponding rotation of the object holder 8) the second surface region 61 can be imaged using the electron beam 55 or the ion beam 50. Alternatively, or as an addition thereto, provision is made for introducing the object 4 into a TEM and examining the first surface region 60 and/or the second surface region 61 of the object 4 in more detail using the TEM. The object 4 is penetrated by an electron beam in the TEM.

The first part 53 of the first contrast-agent layer 52A and the first part 53 of the second contrast-agent layer 52B can be localized. By way of example, the distribution of the first part 53 of the first contrast-agent layer 52A and/or the first part 53 of the second contrast-agent layer 52B can be illustrated three-dimensionally by producing and examining a number of slices of the object 4.

In an alternative embodiment of the exemplary embodiment illustrated in FIG. 6, the image contrast in the image is additionally determined by imaging the object 4 a number of times in succession using the electron beam 55, as already explained previously.

The image contrast may also be established, by further spectroscopic methods in all embodiments of the system described herein. Additionally, or as an alternative thereto, provision is made for leaving the contrast-agent layer 52, 52A, 52B on the surface 56, 56A, 56B for a prescribable amount of time, which has already been established, in order to obtain a specific image contrast. By way of example, the prescribable amount of time is determined on the basis of previously established empirical values from earlier measurements, wherein values for the prescribable amount of time for obtaining a specific image contrast are stored in a database and can be read out.

Controlling the temperature of the object 4 using the heating device 46 can also influence the diffusion.

In all of the aforementioned exemplary embodiments, an ion beam 50 or a light beam 47 is used for depositing a contrast agent. However, reference is explicitly made to the fact that a particle beam in the form of an electron beam can also be used for depositing the contrast agent.

In a further embodiment of the system described herein, the exemplary embodiment in FIG. 6 is combined with the exemplary embodiment in FIG. 3. Thus, a first region with a contrast-agent layer and a second region without contrast agent are arranged on the first side 63 of the object 4 using the described method. The same is provided for the second side 64 of the object 4. The method steps are carried out analogously to the exemplary embodiments as per FIGS. 3 and 6.

In yet another embodiment of the system described herein, the exemplary embodiment in FIG. 6 is combined with the exemplary embodiment in FIG. 4 or in FIG. 5. Thus a first region with a contrast-agent layer and a second region with a protective layer are arranged on the first side 63 of the object 4 using the above-described method. The same is also provided for the second side 64 in this case. The method steps are carried out analogously to the exemplary embodiments as per FIGS. 4 and/or 5 and 6.

In all embodiments of the system described herein, the contrast-agent layers 52, 52A and 52B may be removed not completely, but only partially such that a certain layer thickness of the contrast-agent layers 52, 52A and 52B remain on the object 4. This does not immediately stop the diffusion into the object 4. What is advantageous is that structures lying under the contrast-agent layer 52, 52A and 52B can be imaged in an improved fashion. In a further embodiment, provision is made for the contrast-agent layers 52, 52A and 52B to be removed, at least partially or possibly completely, only locally from a very specific point on the object 4. Hence the contrast-agent layers 52, 52A and 52B remain on the object 4 except for on this very specific point.

Various embodiments discussed herein may be combined with each other in appropriate combinations in connection with the system described herein. Additionally, in some instances, the order of steps in the described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable medium and executed by one or more processors. The computer readable medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible storage medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for producing images of a specimen, comprising:
   introducing a specimen having a surface into a specimen chamber of a charged particle-beam device;
   scanning the specimen with a charged particle beam to generate a first image of the surface of the sample;
   selecting specific positions on the surface of the specimen based on the first image;
   supplying a gaseous metal precursor to the specific positions on the surface of the specimen;
   providing a noble gas ion beam;
   guiding the noble gas ion beam onto the specific positions on the surface of the specimen;
   applying a metal layer to the specific positions on the surface of the specimen as a result of the interaction of the noble gas ion beam with the gaseous metal precursor;
   supplying a gaseous contrast-agent precursor into the specimen chamber, the contrast-agent precursor forming a contrast agent layer on the surface of the specimen;
   leaving the contrast-agent layer on the surface of the specimen for a predetermined amount of time, wherein, during the predetermined amount of time, a first part of the contrast-agent layer diffuses into the specimen, and wherein a second part of the contrast-agent layer remains on the specimen;
   after the predetermined amount of time, removing the second part of the contrast-agent layer and the metal layer from the surface of the specimen; and
   scanning the specimen with the charged particle beam a second time to generate a second image of the surface of the sample.

2. The method according to claim 1, further comprising at least one of the following:
   (i) applying the metal layer with a layer thickness of up to 1000 nm,
   (ii) applying the metal layer with a layer thickness of up to 100 nm,
   (iii) applying the metal layer with a layer thickness of up to 50 nm,
   (iv) applying the metal layer with a layer thickness of up to 10 nm,
   (v) applying the metal layer with a layer thickness of up to 5 nm, (vi) applying the metal layer with a layer thickness of up to 1 nm,
(vii) applying the metal layer to the surface of the specimen in at least one predefinable region of up to 1000 μm around the specific positions,
(viii) applying the metal layer to the surface of the specimen in at least one predefinable region of up to 500 μm around the specific positions,
(ix) applying the metal layer to the surface of the specimen in at least one predefinable region of up to 250 μm around the specific positions,
(x) applying the metal layer to the surface of the specimen in at least one predefinable region of up to 50 μm around the specific positions,
(xi) applying the metal layer to the surface of the specimen in at least one predefinable region of up to 25 μm around the specific positions, or
(xii) applying the metal layer to the surface of the specimen in at least one predefinable region of up to 5 μm around the specific positions.

3. The method according to claim 1, wherein the charged particle beam is guided away from the surface after forming the contrast-agent layer.

4. The method according to claim 1, further comprising at least one of the following:
(i) determining an image contrast,
(ii) determining an image contrast from an image recorded using a spectroscopic method,
(iii) determining an image contrast from an image recorded using the charged particle beam, or
(iv) determining an image contrast from an image recorded using a light beam.

5. The method according to claim 4, wherein the surface of the specimen is imaged a number of times in succession using at least one of: an optical device, a particle-optical device or the charged particle beam, in order to determine a change in the image contrast over time.

6. The method according to claim 1, wherein a temperature of the specimen is controlled in order to influence the diffusion of the contrast-agent layer into the specimen.

7. The method according to claim 1, wherein the charged particle beam has one of the following characteristics:
(i) an energy of less than or equal to 1 keV,
(ii) is an ion beam, or
(iii) is an electron beam.

8. The method according to claim 7, wherein the charged particle beam is a noble gas ion beam.

9. The method according to claim 8, wherein the noble gas ion beam is an argon ion beam.

10. The method according to claim 1, wherein the charged particle beam is a first particle-beam, wherein a second particle beam is provided, and wherein at least one of: forming the contrast-agent layer or the removal of a part of the contrast-agent layer is observed by imaging the specimen using the second particle beam.

11. The method according to claim 10, wherein the second particle beam is an electron beam.

12. The method according to claim 1, wherein at least one of the following is provided:
(i) the contrast-agent precursor is supplied as gaseous osmium tetroxide or as gaseous ruthenium tetroxide,
(ii) a protective layer is applied to the surface of the specimen.

13. The method according to claim 1, wherein the contrast agent-layer is formed only on the specific positions or a local region of the specific positions.

14. A method of producing images of a specimen, comprising:
introducing a specimen having a surface into a specimen chamber of a charged particle-beam device;
scanning the specimen with a first charged particle-beam to generate a first image of the surface of the specimen;
selecting specific positions on the surface of the specimen based on the first image, the specific positions forming a partial region of the surface of the specimen;
supplying a gaseous contrast-agent precursor into the specimen chamber, the contrast-agent precursor forming a contrast agent-layer at least on the specific positions;
after supplying the gaseous contrast-agent precursor, providing at least one of: a second charged particle beam or a light beam onto the specific positions;
after providing the at least one of: the second charged particle beam or the light beam onto the specific positions, scanning the specimen with the first charged particle beam a second time to generate a second image of the surface of the sample;
leaving the contrast-agent layer on the surface of the specimen for a predetermined amount of time, wherein, during the predetermined amount of time, a first part of the contrast-agent layer diffuses into the specimen, and wherein a second part of the contrast-agent layer remains on the specimen; and
removing the second part of the contrast-agent layer partly or wholly without damaging structures on the surface of the specimen to be imaged using at least one of: the first or the second charged particle beam, and wherein the first part of the contrast-agent layer remains in the specimen.

15. The method according to claim 14, further comprising at least one of the following:
(i) forming the contrast-agent layer on the surface of the specimen in at least one predefinable region around the specific positions,
(ii) forming the contrast-agent layer on the surface of the specimen in at least one predefinable region of up to 1000 μm around the specific positions,
(iii) forming the contrast-agent layer on the surface of the specimen in at least one predefinable region of up to 500 μm around the specific positions,
(iv) forming the contrast-agent layer on the surface of the specimen in at least one predefinable region of up to 250 μm around the specific positions,
(v) forming the contrast-agent layer on the surface of the specimen in at least one predefinable region of up to 50 μm around the specific positions,
(vi) forming the contrast-agent layer on the surface of the specimen in at least one predefinable region of up to 25 μm around the specific positions, or
(vii) forming the contrast-agent layer on the surface of the specimen in at least one predefinable region of up to 5 μm around the specific positions.

16. The method according to claim 14, further comprising at least one of the following:
(i) forming the contrast-agent layer with a layer thickness of up to 1000 nm,
(ii) forming the contrast-agent layer with a layer thickness of up to 100 nm,
(iii) forming the contrast-agent layer with a layer thickness of up to 50 nm,
(iv) forming the contrast-agent layer with a layer thickness of up to 10 nm, (v) forming the contrast-agent layer with a layer thickness of up to 5 nm, or
(vi) forming the contrast-agent layer with a layer thickness of up to 1 nm.

17. The method according to claim 14, wherein the contrast agent-layer is formed only on the specific positions or a local region of the specific positions.

18. The method according to claim 14, wherein at least one of: the first charged particle beam, the second charged particle beam or the light beam is guided away from the surface after forming the contrast-agent layer.

19. The method according to claim 14, further comprising at least one of the following:
(i) determining an image contrast,
(ii) determining an image contrast from an image recorded using a spectroscopic method,
(iii) determining an image contrast from an image recorded using the first charged particle beam or the second charged particle beam, or
(iv) determining an image contrast from an image recorded using the light beam.

20. The method according to claim 19, wherein the surface of the specimen is imaged a number of times in succession using at least one of: an optical device, a particle-optical device, the first charged particle beam or the second charged particle beam, in order to determine a change in the image contrast over time.

21. The method according to claim 14, wherein a temperature of the specimen is controlled in order to influence the diffusion of the contrast-agent layer into the specimen.

22. The method according to claim 14, wherein the first charged particle beam or the second charged particle beam has one of the following characteristics:
(i) an energy of less than or equal to 1 keV,
(ii) is an ion beam,
(iii) is a noble gas ion beam,
(iv) is an argon ion beam, or
(v) is an electron beam.

23. The method according to claim 14, wherein at least one of the following is provided:
(i) the contrast-agent precursor is supplied as gaseous osmium tetroxide or as gaseous ruthenium tetroxide,
(ii) the light beam is a laser beam,
(iii) the light beam is UV light,
(iv) the light beam is UV light having a wavelength of between 1 nm and 400 nm, or
(v) a protective layer is applied to the surface of the specimen.

24. A method of producing images of a specimen, comprising:
introducing a specimen having a surface into a specimen chamber of a charged particle-beam device;
scanning the specimen with a first charged particle-beam to generate a first image of the surface of the specimen;
selecting specific positions on the surface of the specimen based on the first image, the specific positions forming a partial region of the surface of the specimen;
supplying a gaseous contrast-agent precursor into the specimen chamber, the contrast-agent precursor forming a contrast agent-layer at least on the specific positions;
after supplying the gaseous contrast-agent precursor, providing at least one of: a second charged particle beam or a light beam onto the specific positions;
after providing the at least one of: the second charged particle beam or the light beam onto the specific positions, scanning the specimen with the first charged particle beam a second time to generate a second image of the surface of the sample,
wherein the surface of the specimen is imaged a number of times in succession using at least one of: an optical device, a particle-optical device, the first charged particle beam or the second charged particle beam, in order to determine a change in the image contrast over time, and
wherein a part of the contrast-agent layer is partly or wholly removed using at least one of: the first or the second charged particle beam, and wherein another part of the contrast-agent layer remains in the specimen, and wherein the imaging takes place before the whole or partial removal of the part of the contrast-agent layer.

25. The method according to claim 24, wherein the whole or partial removal of the part of the contrast-agent layer takes place as soon as the image contrast exceeds a predefined threshold.

26. The method according to claim 24, wherein the contrast agent-layer is formed only on the specific positions or a local region of the specific positions.

27. The method according to claim 24, wherein at least one of: the first charged particle beam, the second charged particle beam or the light beam is guided away from the surface after forming the contrast-agent layer.

28. The method according to claim 24, wherein a temperature of the specimen is controlled in order to influence the diffusion of the contrast-agent layer into the specimen.

29. The method according to claim 24, wherein the first charged particle beam or the second charged particle beam has one of the following characteristics:
(i) an energy of less than or equal to 1 keV,
(ii) is an ion beam,
(iii) is a noble gas ion beam,
(iv) is an argon ion beam, or
(v) is an electron beam.

30. The method according to claim 24, wherein at least one of the following is provided:
(i) the contrast-agent precursor is supplied as gaseous osmium tetroxide or as gaseous ruthenium tetroxide,
(ii) the light beam is a laser beam,
(iii) the light beam is UV light,
(iv) the light beam is UV light having a wavelength of between 1 nm and 400 nm, or
(v) a protective layer is applied to the surface of the specimen.

* * * * *